United States Patent

Matsumura et al.

Patent Number: 5,270,207
Date of Patent: Dec. 14, 1993

[54] CIRCULATORY CULTURE EQUIPMENT

[75] Inventors: Toshiharu Matsumura; Yasuko Sawai; Jun Suzuki, all of Odawara; Takao Fuzimori, Tokyo, all of Japan

[73] Assignee: Meiji Milk Products Company Limited, Tokyo, Japan

[21] Appl. No.: 663,936

[22] PCT Filed: Jun. 26, 1990

[86] PCT No.: PCT/JP90/00831
§ 371 Date: Feb. 22, 1991
§ 102(e) Date: Feb. 22, 1991

[87] PCT Pub. No.: WO91/00339
PCT Pub. Date: Jan. 10, 1991

[30] Foreign Application Priority Data

Jun. 26, 1989 [JP] Japan ................. 1-160621
Jun. 25, 1990 [JP] Japan ................. 2-166125

[51] Int. Cl.$^5$ ................................. C12M 3/04
[52] U.S. Cl. ........................... 435/285; 435/310; 435/315; 435/316; 435/813
[58] Field of Search .................... 435/284-286, 435/288, 299, 310, 311, 313, 315, 316, 813, 818; 210/150, 151, 617, 629

[56] References Cited

U.S. PATENT DOCUMENTS

| | | |
|---|---|---|
| 3,523,763 | 8/1970 | Van Driesen et al. |
| 3,617,541 | 11/1971 | Pan ........................ 210/150 |
| 3,966,599 | 6/1976 | Burkhead .................. 210/151 |
| 3,980,561 | 9/1976 | Miyagi et al. ............. 210/151 |
| 4,454,038 | 6/1984 | Shimodaira et al. ........ 210/150 |
| 4,940,540 | 7/1990 | McDowell ................. 210/150 |

FOREIGN PATENT DOCUMENTS

| | | | |
|---|---|---|---|
| 3302436 | 8/1983 | Fed. Rep. of Germany | 435/315 |
| 0041455 | 3/1977 | Japan | 210/150 |
| 0021855 | 2/1978 | Japan | 210/151 |
| 0030159 | 3/1978 | Japan | 210/151 |
| 0032959 | 3/1978 | Japan | 210/151 |
| 0064951 | 6/1978 | Japan | 210/151 |
| 2003784 | 1/1987 | Japan | 435/288 |

Primary Examiner—Michael G. Wityshyn
Assistant Examiner—William H. Beisner
Attorney, Agent, or Firm—Pennie & Edmonds

[57] ABSTRACT

A culture equipment for bio-organisms such as animal cells and plant cells, having substratum and a circulation-inducing chamber, accommodating the material for substratum made of fibrous, or porous, or layered substance, such as of ceramics, plastics, resin or skin having a number of spaces in the substratum for adhesion or immobilization of microorganisms and medium permeation in the lid-containing vessel, and circulating the culture medium by a rotater device in the circulation-generating room is described in the present invention. The gas exchange of the culture medium is performed in the upper part of the vessel in the course of circulation. Growth and maintenance of micro-organism cells in mass and at a high density can be attained.

9 Claims, 7 Drawing Sheets

FIG. 4
FIG. 2(1)
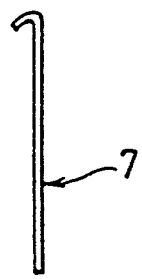
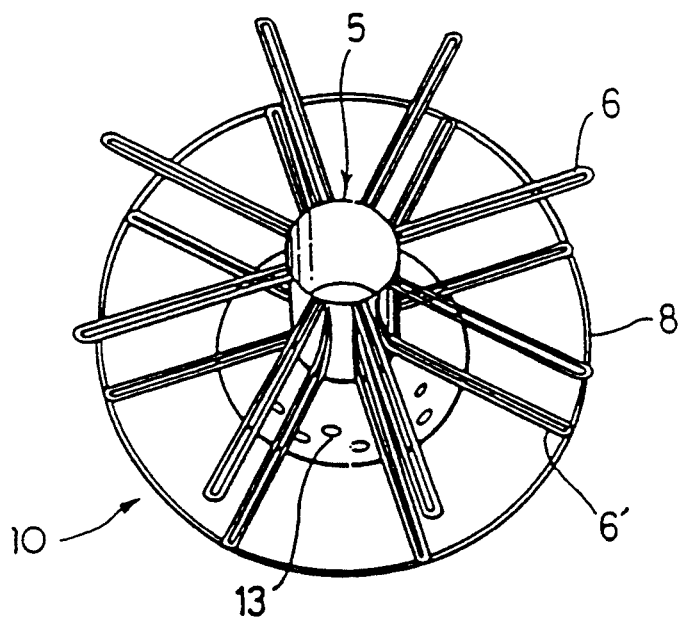

F I G. 3 (2)

CIRCULATORY CULTURE EQUIPMENT

FIELD OF THE INVENTION

This invention is concerned with culture equipment to make a mass culture of bio-organisms including animal cells, human cells, higher plant cells and cells of micro-organisms such as algae, and to maintain the cultured cells in a high density for a long period of time. In additional, this invention is concerned with devices for cell culture and cell maintenance which can be applied to culture equipment for the production of secreted substances and of cellular substances, and to bioreactors for metabolism and extracorporeal artificial organs.

BACKGROUND OF THE INVENTION

High industrial value is widely recognized in the production of substances from animal cells including human cells. They include such substances with wide use for medicine and reagenets as viral antigenic proteins from virus-infected cell, interferons, cytokines, growth factors, monoclonal antibodies, and tissue plasminogen activator.

In addition, mass cells themselves, such as cultured skin keratinocytes, endothelial cells, liver cells and pancreatic Langerhans cells are of great value, since they have successfully been applied in therapy in such ways or forms as skin grafting, hybrid-type artificial blood vessels, artificial organs and transplantation in experimental level. A particular example of success in experimental level is the application of a mass culture of liver cells in the replacement of liver function: A mass culture of liver cells in a vessel, which is connected to a living body from outside through artificial blood vessel, works as an extracorporeal liver, and is expected to overcome liver disfunction in an acute stage.

Technological needs therefore exist in the methods and devices to obtain a mass culture of such bio-organisms as animal cells including human cells, as well as to maintain cultured cells for a long time in a high cell density.

Below, related art is described exemplifying the methods of animal cell culture with the purpose of substance production.

(1) Stationary monolayer culture method.

In this method, cells are cultivated in the state that cells adhere, either actively or passively, to the surface of flat substratum, such as glass and plastics. Plastic culture bottles have widely been used. The use of culture vessels, each with a large surface of multi-layered plastic plates settled in a cuboid module, is the representative technique of mass cell culture (Weiss, R. S. & Schleicher, J. B., Biotech. Bioeng. 10:601–616 (1968). The technique using this type of culture vessel is generally operated with batch culture method, i.e., a method in which cells inoculated in a vessel are fed with culture medium for a period of time, and then the culture is terminated yielding cells and spent medium. Although being the most basic method of mass cell culture for adherent cells, this method has such restriction that the number of cells cultivated is relatively small per volume of culture vessel, that man power for handling culture vessels and feeding cells is large, and that a culture vessel is costive, if it is disposable.

(2) Movable monolayer culture method

In this method, a culture vessel is moved, or rotated while cells grow in a monolayer. This method partially solved problems associated with the stationary monolayer culture method. Using various mechanical means, feeding cells with gas and nutrient has become efficient. The area of substrate surface can be increased extensively. This method is exemplified by a technique (Roller bottle culture method) in which the cell monolayer is formed in the internal surface of a rolling cylindric culture bottle (roller bottle). A number of modifications of the roller bottle culture method have been attempted in order to increase cell density per device volume. In one example, a sheet of wavy plastic thin plate and a sheet of flat plastic thin plate are alternatively rolled in within the interior of the roller bottle (Sterilin, Bulk Culture Vessel, Sterilin Ltd., Teddington, Middlesex).

The movable monolayer culture method is for increasing the contact of cells with culture medium and gas phase by rotating the culture device itself, or culture substratum, and thus has no relation to the present invention, which essentially is a culture method for a flowing culture solution with the substratum fixed.

(3) Micro-carrier culture method.

In this method, cells are made attached onto, or penetrated into micro-particles, which are suspended in liquid medium by mechanical force. Thus, cells are cultivated while they are attached on or in the floating micro-particles in suspension. Many kinds of micro-particle carriers (micro-carrier) have been devised for use in this technique. Particular attention has been given to developing micro-carriers, suitable for weakly adhesive cells to attach to and for cells to penetrate (Van Wezel, A. L., Nature, 216:64–65 (1967), Van Wezel, A. L. in Animal Cell Biotechnology, ed. by Spier, R. E. & Griffith, J. B., Academic Press, London, Vol. 1, 265–282 (1985)).

A vessel of micro-carrier suspension provides a surface area for cell adhesion much larger than a vessel of either the stationary or movable monolayer culture. With this advantage, the micro-carrier culture method becomes a standard technique for mass cultivation of adherent cells. To maintain micro-carrier particles in a suspended state, impellers, rotators, and the introduction of floating bubbles are used. While representative of methods for mass cultivation which are universally used for adherent cells, despite its disadvantages in the difficulty in keeping micro-carriers in a homogeneous suspension or in damages against cells, the micro-carrier culture method the Press has no relation to invention: In the micro-carrier culture method, the substratum itself is floated and agitated: However, in the present invention, although the micro-carrier can be used as substratum, only the liquid medium is flowed.

(4) Cell culture method using hollow fiber.

In this method a device similar to artificial kidney for dialysis use is employed. The device is composed of a bundle of many tubular semipermeable threads or hollow fibers in a columner case.

Cells are locked in the space between the hollow fibers, while liquid medium is circulated in the semipermeable hollow fiber in order to supply nutrient to the cells and to make gas exchange through the tubular thread. Thereby, a cell density near to that in vivo can be realized (Knazek, R. A., Gullino, P. M. Kohler, P. O. & Science, 178:65–66 (1972), Tyo, M. A., Bulbulian B. J., Menken B. Z., Murphy, T., J. Animal Cell Biotech. 3:357–371 Academic Press, London (1988)).

In addition, cells non-adhering to the hollow fiber can be cultivated, since they can simply be stacked between bundles of filers. Although being modern and frequently used, the hollow fiber culture method has no relation to the present invention. In the hollow fiber culture method, the essential technique is characterized by the compartment for cells and the compartment for circulating liquid medium being separated by the semipermeable membrane of capillary tubular thread. Although hollow fibers can be used as substratum for the present invention, other substratum can also be used regardless of the semi-permeability of the fibers.

(5) Immobilized cell culture method.

In this method, the feeding of cells with a nutrient medium, gas exchange, and the removal of waste products are performed by a flowing liquid. The cells are immobilized in or on the surface of a substratum, which permits cells to adhere, or the medium to permeate. Since such common products as matrix glass fiber and ceramic monolith can be used as substrata, and since weakly adhesive cells can be immobilized, this method provides a wide range of application.

Among techniques belonging to this culture method, widely used is that for a perfusion culture equipment (Opticell ® culture equipment). In the Opticell ® culture system, medium flows through a pump into a jacket with a porous ceramic module incorporated (Opticore ®, in which cells are immobilized. The medium flowing out from the module is further circulated through the channels of a gas exchanger, medium reservoir, monitoring devices, etc. (Lydersen, B. K., Pugh, G. G., Paris, M. S., Sharma, B. P., & Noll, L.A.P. Biotechnology 3: 63-67 (1985)).

The present invention falls under the category of immobilized cell culture method in general. However, it has no relation to the prior arts including the Opticell ® culture method. That is, the present invention is concerned with a type of culture device and related techniques of a culture method. While it is capable of incorporating all materials including porous ceramic module, glass fiber etc. after being worked into the water-permeable and cell-immobilizable form as substratum, it does not target to specify substratum.

(6) Suspension culture method.

In this method, weakly adherent cells are cultivated in a floating state in a liquid medium. In principle, the method is identical to suspension culture of mircoorganisms. For the case using animal cells, various devices have been installed to prevent damages to cells caused by shearing force which happens during agitating culture medium. The method is widely used for modern mass culture. The method, however, has no relation to the present invention which is generally in the category of immobilized cell culture.

The conventional cell culture methods described above are associated with problems described below.

(1) Cell damage.

To maintain cells in a floating state, mechanical force is applied from outside, which inevitably creates a shearing force on the cells. This shearing force gives rise to critical problems in suspension cultures, or micro-carrier cultures of animal cells which lack a cell wall, and are easily damaged by shearing force. This damage becomes a critical factor preventing scaling up of culture volume, and in enhancing cell density.

(2) Long-term maintenance of a culture.

Long-term maintenance of a culture is frequently difficult due to the wear and tear of the culture vessel, substratum and mechanical elements, and due to the changes of culture environment along with the accumulation of cellular substances and/or dead cells.

Actual problems along with a long term culture are as follows: In monolayer cultures, cell layers peel-off. In suspension cultures, cell separation apparatus and gas exchange apparatus clog with aggregates of cells. In micro-carrier cultures, micro-carriers flocculate, and cells exfoliate. In perfusion cultures such as hollow fiber cultures and immobilized cell cultures, increasing load to pumps often causes an unexpected shut down.

(3) Generality of culture methods.

Conventional culture methods are frequently applied only to restricted cell species depending on the existence, non-existence, or the strength of cell adherence. For example, the micro-carrier culture method and movable monolayer culture method require strong adherence of cells to the substratum. On the contrary, adherent cells can not usually be cultivated in suspension culture.

(4) Gas exchange

The efficiency of gas exchange in supplying oxygen for consumption and in removing carbon dioxide produced during cellular metabolism is a critical factor limiting the density of cultured cells.

In fact, in the stationary monolayer culture method, low efficiency in aeration on the surface of the substratum is one of the major critical factors limiting cell multiplication.

In suspension cultures, introduction of the technique for sparging air bubbles in a liquid medium has increased the efficiency of gas exchange greatly. This technique, however, also introduced some problems when applied to animal cell cultures: At the surface of air bubbles, medium proteins tend to denature and cells are damaged.

These problems have been partially solved by introducing a method to supply gas through gas-permeable tubes arranged in the culture medium.

It is now possible with gas-permeable tubes to exchange gas with a very high efficiency. In a long term cell culture, however, gas-permeable tubes should frequently be changed since gas exchange efficiency decreases due to the clogging of the surface of the tubes.

(5) The separation of cells from liquid culture medium and the supply of medium nutrients.

Cell separation in suspension culture method and micro-carrier culture method is carried out with natural precipitation, centrifugation or membrane separation. In a large scale cell culture, cell separation devices are introduced to remove waste medium, and to collect cells or cell-adhered micro-carriers, utilizing differences in density between cells, or cell-adhered micro-carriers and the culture medium.

The separation of cells from liquid culture medium is usually not a problem for stationary monolayer culture method or a culture method with the state of cells adhered to substratum. In contrast, with the suspension cell culture method or the micro-carrier culture method, the clogging and decreasing performance of separation apparatus are important matters. With modern systems advancing into those permitting high cell density, where high performance and long life separation apparatus are required, cell separation methods are thus becoming very important.

(6) Effect on purification process.

In a cell culture system in which a cell product is discharged into culture medium, the load on the purification step varies considerably according to the kind of substances other than the product contained in culture medium. In a culture system which causes a considerable damage to cells, for example, large amounts of proteins and DNA are discharged from damaged cells into the culture medium, causing an increase in the load on the purification step.

(7) Reliability of culture equipment.

With the advancement in performance of cell culture equipment, more and more parts are becoming needed for the construction and operation thereof. In addition to such main parts as a culture vessel and substratum for the cell culture, there are a number of parts, some of which are mentioned below, for example: rotators, stirrers, impellers or vibrators, pumps and their driving parts, cocks, tubes, removable connectors for mechanical parts; and oxygen electrodes, pH electrodes, carbonic acid gas electrodes, pressure sensors, and temperature sensors for monitoring parts.

In addition to these parts, there are gas supply apparatus, condensers and filters for exhausted gas, suppliers of constant temperature water, suppliers of desterilized liquid medium, sterilizing apparata for systems, and automated control installation to combine total systems.

Complication of the system is inevitable. Accordingly, associated problems, i.e., the high cost of culture equipment, the decrease in reliability in mechanical terms, and the insecurity of long term operation, are posed as decisive factors with the modern large scale cell culture systems.

(8) Economy of cell culture

With the purpose of substance production by cell culture, important factors in terms of economy are in the reliability, the cost and the scale of culture equipment. Call density achieved is also an important matter. For reference, the maximum density of cells achieved is as follows: In conventional suspension cultures or stationary monolayer cultures, it is in the order of $n \times 10^6$ cells/cm$^3$; in micro-carrier cultures, it is in the order of $n \times 10^7$ cells/cm$^3$; in hollow fiber cultures, it is close to $10^8$/cm$^3$. An achievement of high density near $10^8$ cells/cm$^3$ is a current target, since there is a competitive alternative choice of production system, i.e. in vivo transplantation of hybridoma cells into animals.

SUMMARY OF THE INVENTION

An object of the present invention is to provide an equipment capable of cultivating animal cells including human cells, plant cells and the cells of micro-organism including algae with minimum mechanical damage.

A further object of the present invention is to provide a culture equipment durable in a long and stable maintenance.

A still further object of the present invention is to provide a culture equipment applicable to a wide variety of micro-organisms.

Another object of the present invention is to provide a culture equipment capable of performing the exchanges of nutrient components, waste products and gases between micro-organisms and culture medium with ease and high efficiency.

A still another object of the present invention is to provide a culture equipment capable of obtaining the supernatant of culture with less contaminants.

Yet another object of the present invention is to provide a culture equipment capable of achieving the high density of micro-organisms per unit volume of culture medium.

Further another object of the present invention is to provide a culture equipment with reliability in long term operation.

The circulatory culture equipment of the present invention comprises the following parts: The basic part is a culture equipment comprising several sections, namely, culture vessel, substratum, circulation-inducing chamber, circulation-guiding cylinder, and air circulation-guiding plate.

Of these sections, the culture vessel has a removable lid on its top; the substratum is settled on the given position within the culture vessel with appropriate support and provides space for multiplication of microorganisms in an adherent or immobilized condition; the circulation-inducing chamber stores mechanical means to circulate culture medium around the substratum; the circulation guiding-cylinder is set to cover the outside of the aforementioned substratum and; the air stream-guiding plate is settled over the top of substratum.

Other sections constituting the present invention are internal pressure maintaining apparatus, drying apparatus for the exhausting gas filter, culture medium supplying apparatus, driving gear for rotating means, gas supply apparatus, supplying apparatus of constant temperature water, various monitoring and sensoring apparatus, and automated system control installation.

A culture vessel is preferably given a shape with a high ratio of diameter against height, e.g. ca. 2:1, in order to gain high efficiency in the circulation of culture medium. The contacting surface of the bottom and the cylindrical side wall of the culture vessel forms a gentle curve. The lid of the culture vessel allows a flat or arcuate shape. The lid may have mouths for supplying and exhausting gases, for supplying, sampling and removing medium, and for attaching monitoring devices such as an oxygen electrode and temperature sensor. It may also have a sight glass window. A culture vessel can be made of glass, stainless steel, and heat-resistant plastics such as polycarbonate. A glass vessel has the advantage of visibility of the interior.

The substratum is cylindrical or polygonal monolithic in its outward shape, and is provided with a vertical hole, or a flow-down hole, passing through from the top to the bottom of the substratum. It has a number of small vertical holes or open spaces within it, which make it water-permeable as a whole. Thus, culture medium flows up, piercing through a substantial part of said substratum vertically.

The material for the substratum in the present invention can be those having a surface capable of adhering or immobilizing micro-organisms and having certain mechanical strength.

In addition to fabrics or water permeable porous matters such as a ceramic module with honeycomb structure, usable materials include non-woven fabrics, bundles of capillary tubes, materials with layered structure or a honeycomb structure made of fibers (glass fiber, animal and plant fiber, synthetic fibers), porous matters (glass, plastics), and films. In necessity, increased capability of adhesion or immobilization of micro-organisms is provided by a treatment of the substratum surface.

A variety of substratum shapes can be designed depending on the material used for substratum. As stated later, an important point here is to make substratum in the form that culture medium can evenly move with a sufficiently high speed within the substratum toward the top, in co-operation with the circulation-inducing chamber, thus maintaining contact of fresh medium with micro-organisms propagating in the substratum. Hence, variations of form of substratum can be made on the basis of the combination with the circulatory apparatus for culture medium mentioned below.

These variations of design can be included in the present invention. With a supporting device, substratum is held in a culture vessel in such a way that the top surface of the substratum is held beneath an air circulation-guiding plate set in the culture vessel, such that the bottom surface of the substratum is held to make connection of said flow-down hole of the substratum to contact with the upper opening of circulation-inducing chamber which contains rotating means and is set on the bottom of culture vessel. The outer surface of the side wall of substratum is held near the inner surface of the side wall of culture vessel.

Supporting devices to hold substratum within culture vessel, as stated above, can be selected depending on the material used for the substratum and are not limited.

In case of woven, or unwoven texture being used for the substratum, the fabric may be cut in a strip form. The one end of the piece is fixed to a tubular cylindric body. Then, the fabric piece is spirally wound, holding a given space with pieces of spacers (explained later) between the texture around the outside of the empty cylindric body, to form a substratum with its size fitting the inner side wall of culture vessel.

In order to maintain the winding distance between the layers of fabric texture, for instance, arms may be arranged radially with a given angle among them both at the top end and at the bottom end of outer side wall of the empty cylindrical body. Then, spacers are inserted into insertion holes displaced in the said arms, and the fabric texture is wound around over the inserted spacers.

After one round of winding, next set of spacers are inserted, and the fabric texture wound around again. When fabric texture is wound up in this way, the spaces between fabrics correspond to the vertical spaces of the substratum, and the mesh of the fabric corresponds to the many small spaces of the substratum, while the empty cylindrical body corresponds to the said flowing-down hole.

A circulation-guiding cylinder, as will be mentioned later, is set in the space held between the inner side wall of the culture vessel and the outer side wall of substratum. In order to stretch the rolled fabric texture, in, screws may be set to pull spacers toward the outside of the arms.

When water-permeable and porous material, such as a honeycomb-like ceramic module are used for the substratum; it is preferably cut out so that small spaces constituting honeycomb pass through vertically, and the horizontal cross section of the substratum fits the inner wall of the vessel.

It is also cut out to make a cylindrical vertical hole for culture medium to flow down. In another way, the substratum with a concentric structure made of ceramics can be used, in which first, empty cylindric bodies are made of ceramics with different diameters, then the bodies of small diameters are orderly inserted in the largest one.

A circulation-guiding cylinder described below should be preferably set in the space provided between the inner side wall of the culture vessel and the outer side wall of the substratum. However, if there is no space, the circulation-guiding cylinder can be omitted.

When a ceramic module is used as the substratum, supporting devices may be needed only to fix the said ceramic module on the top of circulation-inducing chamber within the culture vessel.

As mentioned before, the substratum is contained in, and fixed to the culture vessel with appropriate supporting devices. The circulation-generating room may be directly connected on the bottom end of the hole for downward flow of the culture medium.

The circulation-inducing chamber is set directly beneath the bottom end of the hole for downward of culture medium, and is attached on the bottom surface of the culture vessel, constituting a room to accommodate the circulation-inducing devices.

Thus, the circulation-inducing chamber should have a form relevant to the high speed rotation of liquid in the room.

Possible forms are, for example, a conical trapezoid with a circular transverse section, an inverted bowl or an inverted funnel.

The circulation-inducing chamber has a plurality of holes on its side wall permitting outward flow of the culture medium. The circulation-inducing chamber can be made of such materials as stainless steel, and heat-resistant plastics including polycarbonate.

A rotating device is accommodated in the circulation-inducing chamber so that horizontally free circulation of liquid is generated in the circulation-inducing chamber. The device can be rotated directly by way of a driving device set outside of the culture vessel, or indirectly with a magnet stirrer.

A rotating device can be of various types, such as impeller, rod type rotator, tapered rod type rotator, and discoid rotator. The insertion of a thin plate of glass or stainless steel can protect the bottom surface of the culture vessel in case the rotator touches said bottom.

A circulation-guiding cylinder is set in the space between the inner side wall of culture vessel and the circumference of substratum. The circulation-guiding cylinder covers side circumferential of wall substratum.

The top end of the circulating-guiding cylinder is high enough to prevent inflow of the culture medium between the inner side wall of the culture vessel and the circulation-guiding cylinder onto the culture medium being formed at the time of movement from said top onto the substratum, and should be large enough for its bottom to be located at least in proximity of the bottom of the substratum in the vessel. The top of the circulation-guiding cylinder has a plurality of holes on the level corresponding to the surface of culture medium.

A gas stream-guiding plate has an opening to permit gas passing, and is set in a gas phase space between the surface of the culture medium and the lid of the culture vessel. The gas stream-guiding plate covers the surface of the culture medium at a certain distance. The vertical section of the plate can be given varied shapes corresponding to the shape of the vertical section of said gas phase space. For a small culture vessel, the gas stream-guiding plate can be omitted.

In addition to said apparatus, on occasion, the following apparatus and devices can be used with the culture equipment of the present invention, according to the object or scale of culture: condensers to collect water from exhausted gas; jackets to keep the exhausted gas and the filter for exhausted gas warm in order to prevent condensation of water vapor; tubes and pumps to supply and to discharge culture medium; tubes and pumps to remove the occasionally generated bubbles in the culture vessel; tubes and pumps to supply micro-organisms into the culture vessel; tubes and pumps to obtain samples; oxygen electrodes; pH electrodes; gas permeable tubes set inside of the culture vessel to supply oxygen gas not only through surface aeration but through membrane aeration; gas exchange units set outside of the culture vessel; jackets to keep the culture vessel warm as required and apparatus to supply warm water to the jacket being installed on occasion to the culture vessel; supply sources of compressed oxygen gas, carbon dioxide gas, and air, solenoid valves to adjust gas amounts supplied, and in addition, tubes to connect the supply sources and the valves; internal pressure sensors for the culture vessel and apparatus to prevent overpressure; medium reservoirs to stock new culture medium; reservoirs for spent culture medium; various tubes to connect said apparatus and devices; connectors; switches; electronic control apparatus to control totally those apparatus, devices and things.

In addition, windows can be set to view inside of the culture vessel. If necessary, an air pump or an outerly driven fan can be also set to aid the circulation of gas within culture vessel. As an auxiliary apparatus, an apparatus for sampling cultured cells can be fitted to the present culture equipment. An example is described as follows: A small piece of material, the same as that of the substratum, is attached to, or fused into one end of a glass, ceramic or metal rod. The small piece is then inserted into the interior of the substratum with the other end of the rod hanging by a hook fitted to the culture equipment. When cells are introduced in suspension into the substratum, they also attach to the piece of material.

After an appropriate time of incubation, the pieces can be removed from the hook and out of the culture apparatus under an axenic condition.

The rotating device contained in the circulation-inducing chamber is rotated by a driving force given from the outside of the culture vessel. When the rotation increases sufficiently, the culture medium around the rotating device rotates and imparts centrifugal force to the culture medium. In this way, culture medium gaining a high speed of rotation in the circulation-inducing chamber passes through the many holes opened in the side wall of the circulation-inducing chamber. The medium thus flows evenly from the bottom surface of the substratum into the substratum with a high speed, leading to promotion of the circulation of the medium.

Since the top of the circulation-guiding cylinder is set higher than the level of the culture medium surface being formed during operation of the present culture vessel, the surface level of the culture medium stays in the space between the cylinder and the inner wall of said vessel, higher than on the substratum.

Hence, only the part of culture medium passing through the upper holes of said circulation-guiding cylinder from said space takes part in the circulation. This system is intended to avoid possible uneven conditions in the culture vessel which might otherwise be caused by stagnant culture medium in said space. Consequently, the culture medium in said space eventually flows into the substratum resulting in efficient circulation of culture medium.

When the outer side wall of substratum attaches tightly to the inner side wall of culture vessel, culture medium flowing out from the circulation-inducing chamber at high speed is evenly led to the entire surface of the bottom of the substratum.

The culture medium thus flowing into the narrow vertical spaces within said substratum supplies nutrients to micro-organisms immobilized through or entangled in the substratum. At the same time, the flow in said spaces in the substratum carries useful materials as well as waste materials produced by the micro-organisms to the top surface of the culture medium.

In due course, the culture medium then flows down through a hole opened in a part of the substratum into the circulation-inducing chamber again. It circulates in a given direction repeating the steps mentioned above. As a result, the micro-organisms attached to, or immobilized in the substratum are cultivated.

A high density cultivation of micro-organism can be realized depending on the effective volume of the substratum to immobilize cells, and on the reduction of damage of micro-organisms due to shearing force acting against them.

Furthermore, since cells are attached to, or immobilized on the flat or uneven surface of substratum material, which is kept always in a constant unidirectional flow of liquid medium, the risk that unwanted materials will disturb extraction of useful materials from culture supernatant are reduced. Such unwanted materials are: cell debris, dead bodies of cells, or other cellular substances which float out and are contained in the supernate of the culture.

The use of fibers or materials, with a large amount of irregular surface as substratum material, reduces changes of peeling off of the cells once adhered or immobilized to the substratum. These characteristics make the long term maintenance of the culture possible. In addition, weakly adhesive cells can stay within the substratum easily.

By use of the culture equipment of the present invention with a large amount of running-through spaces in the substratum and with cells adhered to or immobilized in the substratum, it is possible to change the culture medium continuously, and to collect spent medium in a short time period.

The action of gas stream-guiding plate is as follows: In the present invention, gas exchange may be carried out with gas permeable tubes (such as of silicon tubes and porous teflon tubes) installed in the bottom inside, or outside of the culture device in modules. However, often, particularly in a small culture equipment according to the present invention, a sufficient amount of gas exchange is possible simply by surface aeration with the arrangement of the gas stream-guiding plate. The plate helps circulation of gases over the surface of the culture medium with high gas exchange efficiency so that no auxiliary gas exchanger is needed.

In this surface aeration system, after gas flows from a gas supply mouth opened in the lid of the culture vessel into the culture vessel, it hits against the surface of the culture medium. From this point, the gas flows along with the stream of the culture medium between the gas stream-guiding plate and the surface of the culture medium, exchanging gas with the culture medium. The gas then reaches the hole opening on the gas stream guiding plate and the gas running through the hole hits against the lid to be dispersed. While a part of the gas dispersed is exhausted from the exhausting mouth opening in the lid, the rest flows toward the circumference, between the inner surface of the top of culture vessel and gas stream-guiding plate, to hit the inner side surface of the culture vessel. Then again, gas flows toward the hole of the gas stream-guiding plate, and repeats gas exchange between the gas stream-guiding plate and the surface of the culture medium. Thus, gas circulates around both sides of the gas stream-guiding plate, realizing an efficient gas exchange. When gas circulation is forcibly accelerated with an air pump or a driving fan, gas exchange efficiency is further increased by the difference between the flow of the surface of the culture medium and the flow of gas.

The mechanical reliability of the culture equipment of the present invention exceeds that of prior art devices in many respects. While the basic functions of the culture equipment, i.e., the supply and discharge of culture medium, separation of cells from culture medium, gas exchange, and circulation of culture medium, can be carried out using auxiliary outer accessory apparatus, all of these functions can be carried out in a unified culture vessel in the present invention.

As movable parts of the driving body of the liquid transporting pump and the rotator of the pump, a peristalic pump with flexible tubing and a magnet stirrer bar can be employed respectively. Thus, the culture system can be completely closed eliminate the possibility of contamination. Further, in the present culture equipment, it is possible to avoid the use of filters in the separation of cells from the culture medium and in gas exchange, which frequently lack reliability.

With the present culture equipment, high pressure loading can be avoided throughout tubing- and pumping system for the circulation and transportation of the culture medium and gas. Thus, in comparison with other culture methods using filters and auxiliary circulation devices, in the present invention the surface gas exchange method and the method of medium circulation inside the vessel provides the equipment according the invention with a considerably higher reliability and longer life. As summarized above, the culture equipment of the present invention can provide high mechanical reliability to all parts ranging from details to the whole of the culture equipment.

The economy that the culture equipment of the present invention can provide exceeds that of prior art devices in many respects. Reliability relating to economy was mentioned before.

An estimate of cell density to be achieved by the present invention is given as follows: In case when glass fiber is used as substratum material, the surface area is 10 cm$^2$ per 1 cm$^3$, when the distance between layers of glass fiber material is kept 2 mm, and the surface of the glass fiber material is assumed as flat.

For comparison, CELL FACTORY ®, an example of multilayered stationary culture equipment, has the volume of 12 liters per one set of culture equipment, and its surface area for cell attachment is 6,000 cm$^2$. In case of cultivation with a substratum of the same volume in accordance with the present invention, the surface area for cell attachment is 120,000 cm$^2$ per 12 liters. That is, equivalent to that of 20 sets of CELL FACTORY ® in terms of effective surface area of cultivation.

In the case of the culture equipment of this invention, the actual volume of a culture vessel is larger than its substratum volume, since the culture vessel contains accessary apparatus of the invention in addition to the substratum. On the other hand, the effective surface area for cell attachment per unit volume of substratum is expected to be larger in the present invention than as estimated above, since fiber surface has been assumed flat in the estimate, and actual fiber surface is complex.

It is evident, therefore, that the present equipment provides larger adhesion surface area per volume than estimated. In view of the fact that CELL FACTORY ® is a disposable product, the maintenance cost of culture equipment of this invention is very low due to the very low price of the material of consumed parts, such as glass fiber. There is no fundamental difficulty in extending the volume of the present circulatory culture equipment to tens of thousands of cubic meters for such purposes as growing micro-algae by extending the culture system from that for axenic to that for open.

As mentioned above, the culture equipment of the present invention provides superiority to known prior art devices in many respects, including economy.

BRIEF DESCRIPTION OF THE DRAWINGS

The present invention will be described in detail hereinafter with reference to the attached figures, wherein.

DETAILED DESCRIPTION OF THE PREFERRED EMBODIMENTS

Figure 1:
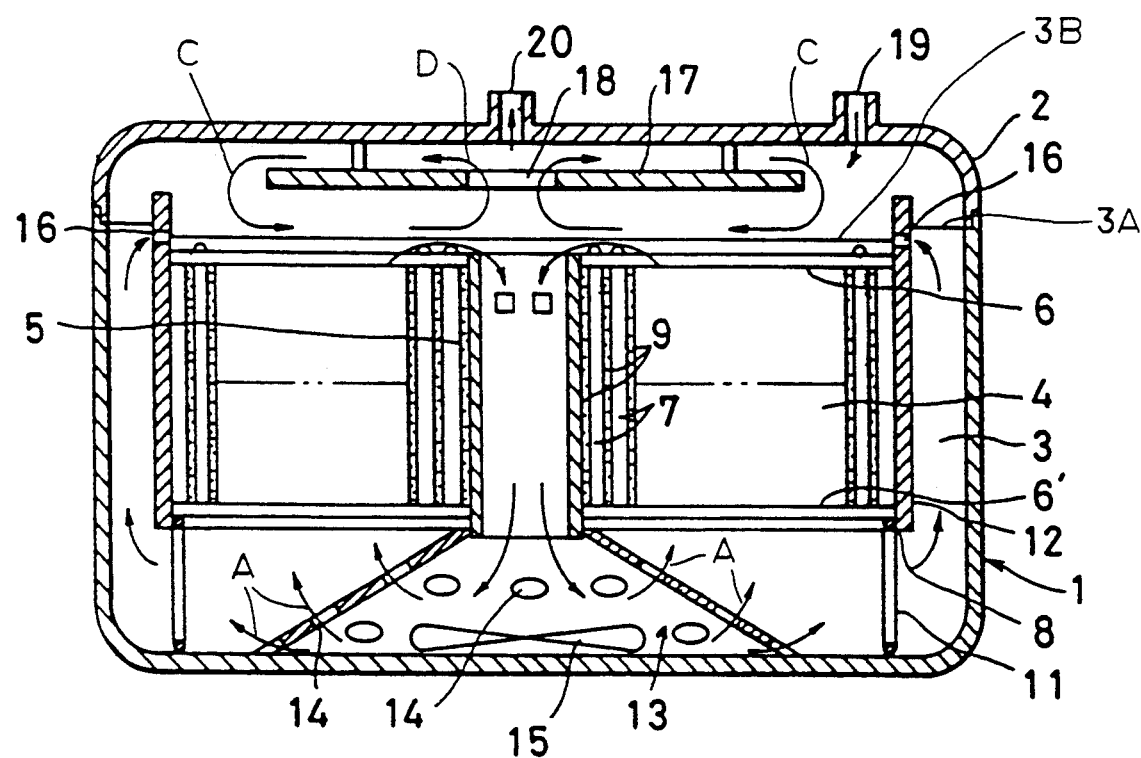
FIG. 1 is a sectional view of an example of the circulatory culture equipment of the present invention.

Hereinafter four examples of preparing culture equipment, namely types 1-4, will be described. In types 1 and 4 (for the preparation of 800 ml culture equipment), glass vessels each with an internal diameter of 105 mm, an internal volume of 1000 ml, and a top lid made of stainless steel, were used. In type 2 (10 liter culture equipment), polycarbonate plastic vessels each with an internal diameter of 30 cm, an internal volume of 10 liter, and a top lid made of stainless steel, were used. In type 3 (50 liter culture vessel), stainless steel vessels, each with an internal diameter of 60 cm, an internal volume of 50 liter, and a top lid made of stainless steel, were used. Hereinafter the four types of the circulatory culture equipment of the present invention will be described in detail with reference to the drawing. All the four types will be described together, since all of them are essentially the same in the shape and construction of the culture vessel.

The shape of the culture vessel 1 is that of a cylinder with a large diameter-to-height ratio, e.g. 2:1 so as to attain efficient circulation of the culture medium 3. The circumference of the bottom surface and cylindrical side wall form a gentle curve to allow smooth circulation of the culture medium. The lid 2 has gas supply mouth 19 and gas exhausting mouth 20, as shown in FIG. 1. The culture vessel 1 can have a jacket (not illustrated) around its circumference if necessary to keep culture vessel 1 warm.

In types 1, 2 and 3 of the culture equipment according to the invention, fabric of glass fiber was used as the material for the substratum. The fabric was a plain weave of bundles of 30 single glass fibers having a thickness of 0.13 mm, woven at 1 mm distance, and with a mass of 75 g/m$^2$.

Figure 2:
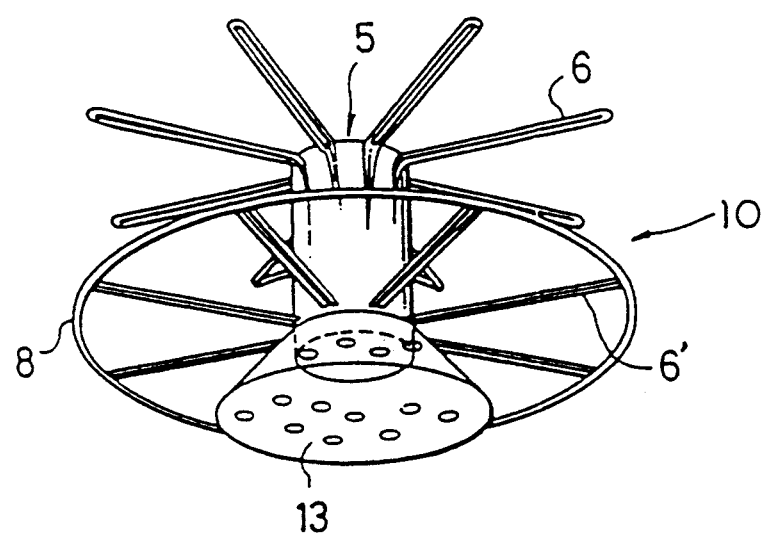
FIGS. 2(1), 2(2), 2(3) one perspective views of supporting devices for the substratum of an example.
Figure 2:
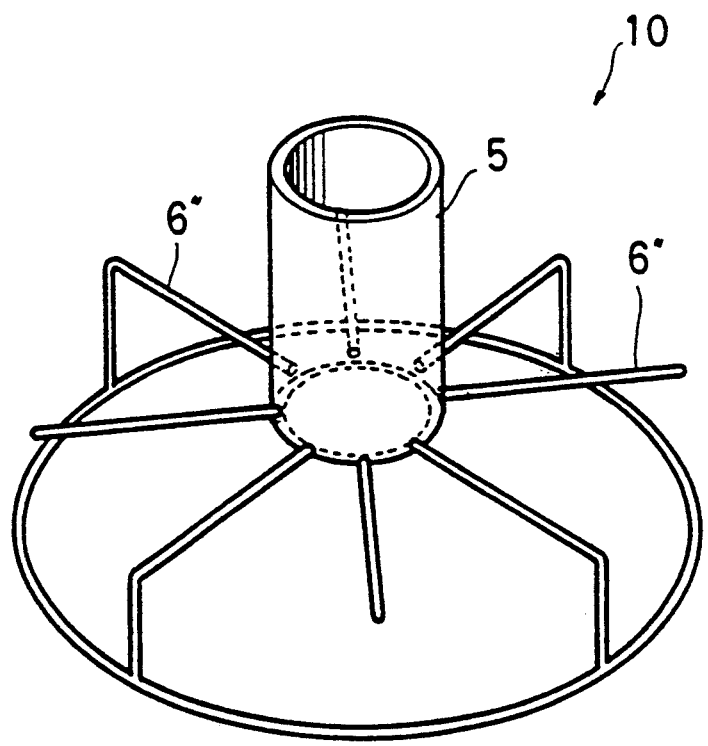
Figure 3:
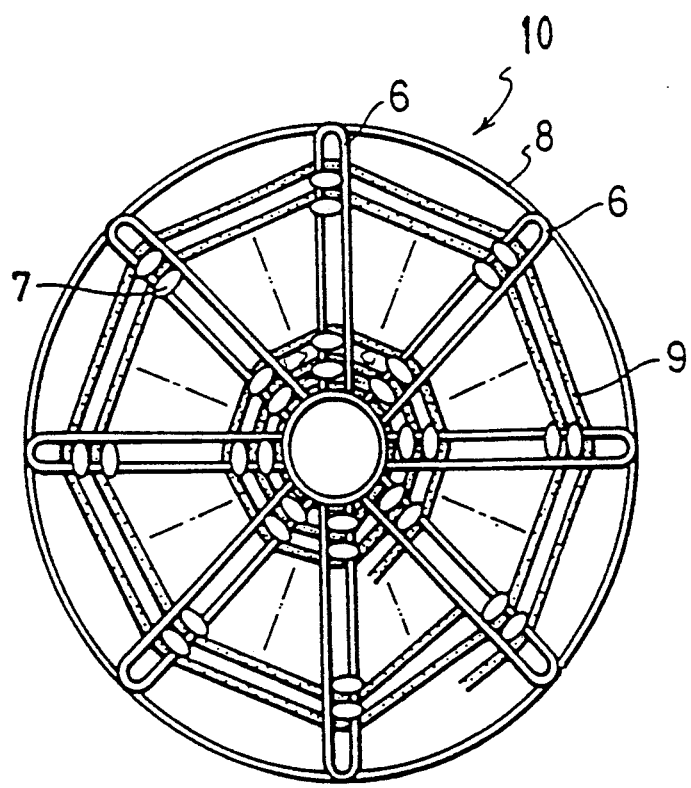
FIGS. 3(1) and 3(2) are plan views of an example of the substratum supporting device with substratum installed.

Within the culture vessel 1, the substratum is made of fabric 9 which is spirally wrapped around the support 10 to make a multilayered structure as shown in FIGS. 3(1). As seen in FIGS. 2(1) and (2), the support 10 of the substratum is provided with arms 6 and 6', extending radially to the corresponding top and bottom ends of the circumferences of the central cylindrical body 5 respectively at a predetermined distance. Ring 8 is provided at the tip of said bottom end.

In both upper and lower arms 6, 6', there are bored guide holes into which spacer 7 can be inserted. Thus, cylindric body 5, including the upper and lower arms 6 and 6', the spacer 7, and the ring 8, is together referred to as substratum support 10. Leg 11 fitting to the bottom end of the ring 8 is installed so as to hold the substratum support 10 steady at a given position in the culture vessel 1. Leg 11 also secure a given distance (the distance which can accommodate the conical circulation-generating room 13 and rotator 15 mentioned later) between the bottom end of the substratum support 10 (where the ring 8 is positioned) and the bottom face.

As described below, in this type, fabric has been attached to the support 10 for substratum as shown in FIG. 3(1). Fabric 9 has approximately the same width as the height between upper and lower arms 6,6'. Fabric 9 is wrapped around the cylinder body 5 to which one end of the fabric is fixed.

Figure 4:
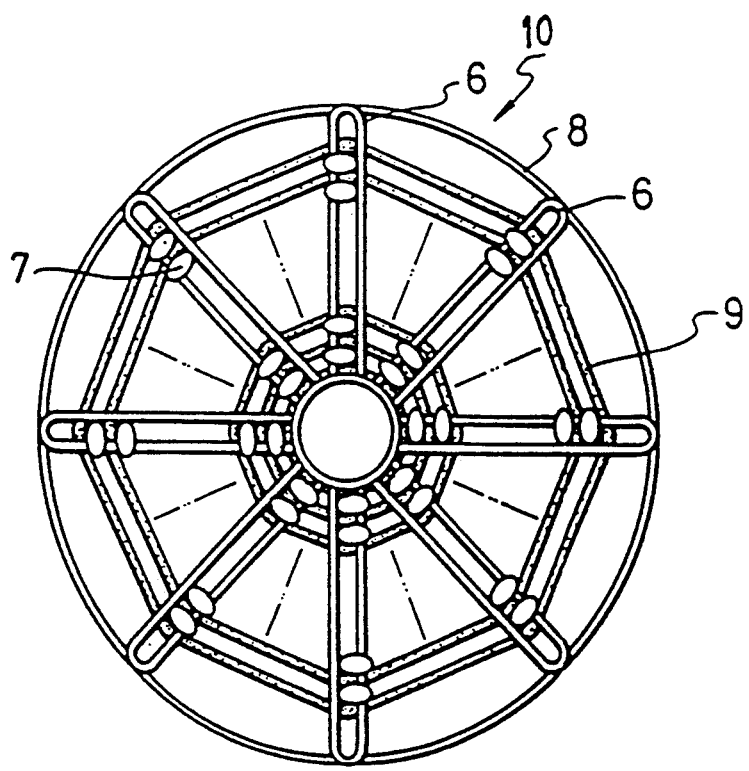
FIG. 4 is a side view of an example of spacer with which the substratum element is held at a given distance.

Then, in the holes of the corresponding upper and lower arms, spacers 7 with the structure shown in FIG. 4 are inserted, and placed against the fabric 9 wrapped around the cylinder body. Then the fabric 9 is wrapped around the inserted spacers 7. These steps are repeated to make substratum 4 comprising the radially wrapped multilayered fabric 9 given a certain distance by the spacer 7 as shown in FIG. 3(1). Circulation inducing chamber 13, having a conical shape, is fixed to the bottom of the cylindrical body 5 of the support 10. The top of the circulation-inducing chamber has an opening with the same diameter as that of cylindrical body 5. The circulation-inducing chamber 13 has several holes 14 on its side wall at evenly spaced intervals. The bottom end of the circulation-inducing chamber touches the bottom of culture vessel 1, surrounding rotator 15.

Rotator 15 is driven to rotate by an outside magnetic stirrer (not illustrated). Circulation-guiding cylinder 12 is fitted around the circumference of substratum 4 to cover the substratum 4. The top end thereof protrudes from the surface of culture medium 3 and the bottom end has a length reaching near the bottom of the substratum 4. Several holes 16 are opened at the upper circumference of the circulation-guiding cylinder 12 at the level corresponding to that of the surface of culture medium 3.

In the gas phase between culture medium 3 and the lid 2 of culture vessel, a discoid gas stream-guiding plate 17 with a hole 18 in its center is arranged to efficiently contact gas phase to the surface of the culture medium.

Figure 5:
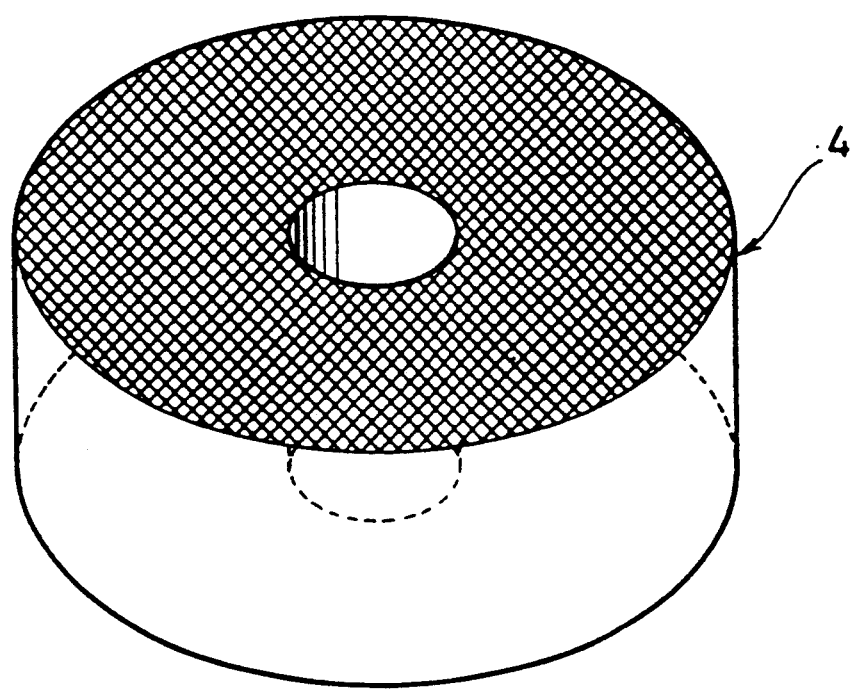
FIG. 5 is an oblique view of another example of substratum.

In example 4 of the present invention, a honeycomb-like ceramic monolith was used as the material of substratum 4 (FIG. 5). The composition of the honeycomb ceramic monolith used was $MgO:Al_2O_3:SiO_2 = 2:2:5$. In the monolith, honeycombs forming a regular quadrangle with a side of 2 mm run vertically through the parallel cylindrical element of 5 cm height and wherein a cylindrical hole of 40 mm in diameter is drilled on the central axis of the cylinder. Stainless-steel cylindrical body with a diameter of 38 mm and height of 55 mm is inserted into this inner hole of the substratum 4 (FIG. 2(3)). Supporting structure 10 was provided, which includes 8 supporting rods (6") in 3.2 cm length equally spaced around the circumference of body 5 and extending in the horizontal direction under the cylindrical body. Stainless steel supports 2 cm in height are attached to respective tips of the supporting rods.

The circulation inducing chamber 13 was fixed to the bottom of the cylindric body 5 in the same manner as in Example 1.

Although sizes differ, the following accessary apparatus were fitted to the lid or the side surface of each embodiment of the culture equipment in Examples 1 to 4: A polarography-type oxygen electrode for each; an interface for each electrode to send values of oxygen pressure to computer; a solenoid valve controlled by a computer according to the value of oxygen pressure; oxygen gas supplying tube with axenic filter and a manual flow meter making the adjustment of flow rate possible; a manual flow meter and a tube and axenic filter to supply air containing $CO_2$ in 5% concentration as the flow rate adjustable gas; a magnetic stirrer; tubing and a peristaltic pump to supply cell suspending solution; tubing and a peristaltic pump to exhaust culture medium; tubing to discharge gas exhausted; warm air supplier to keep gas discharging tube and filter warm and keep them in a dry condition; thermostatic bath and water pump to keep culture vessel warm by passing water into the jacket.

In addition, stainless steel connectors were arranged in necessary positions to fix and remove tubes axenically. Other conditions are partly described in the examples.

The exemplary embodiments of this invention are composed of as mentioned above and therefore act as follows commonly throughout types 1-4:

First, culture medium 3 in the bottom of culture vessel 1 rotates with the rotation of rotator 15 to generate centrifugal force. The rotating speed of the culture medium 3 is efficiently increased around the rotator 15, because the conical-shaped circulation-generating room 13 is installed in the way that it covers the rotator 15.

The culture medium 3, with its speed thus increased, flows evenly substratum 4, after flowing (in the direction of Arrows A) out from holes 14 in the side wall of the conical-shaped circulation inducing chamber 13.

Thus, the culture medium 3 flows into the substratum and up through the substratum 4 supplying the nutrients to cells attached to the substratum 4 and discharging the waste product of the cells. The upward flowing culture medium reaches the top surface of the substratum 4, and overflows into cylindric body 5, as indicated by arrow B. Then, it flows down within the cylindric body 5, returning into the conical-shaped circulation-inducing chamber 13 by virtue of the action of rotator 15. These steps are repeated to enable circulation of the culture medium within substratum 4.

Since the top end of circulation-guiding cylinder 12 is disposed higher than the level of the culture medium 3 during operation, the surface of the culture medium between said cylinder 12 and the culture vessel 1 is higher than the surface of the culture medium over the substratum (at 3B).

However, it is designed so that only the liquid passing through holes 16 drilled in said cylinder 12 takes part in the circulation. The concept of this partial participation in the circulation is made to avoid the difficulty that various conditions within culture vessel 1 become uneven by stagnant culture medium 3 in said space.

The operation of gas stream-guiding plate 17 may be explained as follows. Gas blowing into culture vessel 1 through gas-supplying mouth 19 hits against the surface or culture medium 3, and flows to the center of culture vessel to make gas exchange with culture medium 3. The gas reaching the central region passes through hole 18 opened in the center of gas stream-guiding plate 17 to hit against the lid 2 and to disperse around. Then, the gas flows the direction of arrow D, and a part of the gas is discharged from a mouth 20. At the terminal edge of gas stream-guiding plate 17, the gas flowing in the direction of the arrows D hits both the flow of gas from gas supplying mouth 19 and the inner surface of the culture vessel 1, resulting in the flow into the direction of the arrow C, that is, the circulation around the gas stream-guiding plate 17.

The direction of flow of gas on the surface of culture medium 3 is the same as that of the surface flow of the culture medium 3. Consequently, the circulation of gas enables efficient contact of the surface layer of the culture medium with gas enhancing the efficiency of gas exchange. When the circulation of gas is accelerated forcibly using a pump, gas exchange efficiency increases further.

Hereinafter examples of cell cultures will be described in detail with reference to the experiments.

The culture equipment was used after sterilization using autoclave in their constructed state.

EXAMPLE 1

A culture of various cells was made using the type 1 culture equipment with a fabric made from glass fiber. Culture vessel 1 had a jacket with an internal diameter of 105 mm and depth of 105 mm and a stainless steel lid. The support 10 for the substratum resembled a rack made of stainless steel wire with diameter of 2 mm. Eight arms (top 6 and bottom 6') were arranged radially. Cylindrical body 5 made of stainless steel had 35 mm space between the bottom of the cylindrical body 5 and the bottom surface of the culture vessel 1. Substratum 4 was made of glass fiber fabric 9 with 47 mm width rolled into octagonal shape at 2 mm distance. The substratum had 3 m length and 2,820 cm$^2$ surface area in terms of the area of the fabric. The effective surface area was larger than this value due to the use of glass fiber fabric 9. For conical-shaped circulation-inducing chamber 13 and circulation-guiding cylinder 12, polycarbonate film was used. Gas stream-guiding plate 17 was of a polycarbonate disc with a diameter of 8 cm and hole 18 having a 3 cm diameter. Rotator 15 was rotated at a speed of approximately 800 r.p.m. Through the lid 2 of culture vessel 1, the following five stainless steel tubes in total were distributed: a gas supply tube, a gas exhaust tube, a culture medium supply tube, a culture medium draining tube, and a tube for the supply of cell suspending solution and collection of the samples of culture medium. PH and oxygen electrodes were also arranged in addition.

Monolayer cultures of a line of huH-1 cultured human hepatic cancer cells (Huh, N. and Utakoji, T., Gann, 72, 178-179 (1981)) are grown in plastic dishes using DM160 culture medium supplemented with 5% fetal bovine serum (FBS) as a growth medium. The culture was treated with trypsin to obtain $1.5 \times 10^8$ seed cells. After these cells were placed in the above mentioned culture vessel 1 filled with 800 ml of culture medium for cell multiplication, the culture medium 3 was circulated through the rotation of rotator 15 to attach cell to substratum 4. During first two days the culture medium was not renewed. Within 20 days of total culture duration thereafter, a half of the culture medium was changed on occasion to maintain glucose level and lactic acid level above 300 mg/l and below 500 mg/l, respectively. In the course of cultivation, air supplemented with five percent carbon dioxide gas was aerated at 5-10 ml/min, and oxygen gas was added on occasion. In the culture duration, observation from outside of culture vessel 1 using a stereoscopic microscope was made to find multiplication of cells attaching to substratum 4. After the termination of cultivation, fabric 9 was separated from the support 10 for substratum. The separated fabric was cut into pieces to count cell nuclei using the citric acid-crystal violet staining method. Cell number was $1.05 \times 10^6$/cm$^2$ in terms of the numbers per one side of the fabric 9. The cell number per area is about two times that obtained from monolayer culture using CELL FACTORY ® (Nulgen Co.). The cell number is $1.05 \times 10^7$/cm$^3$ in terms of cell density per volume of substratum 4.

In the culture equipment of type 1 with glass fiber substratum, in addition to the above mentioned human hepatic cancer cell system, a line of C127 I mouse mastocarcinoma cells (Lowry, D. R., Renal, E., Scolnick, E. M.: J. Virol. 26, 291-298 (1978)) of a substrate adherent cell line; a line of KYM-1 human rhabdomyosarcoma cells adapted to grow in suspension culture with slight substrate adherence (Sekiguchi, M., Shiroko, Y., Susuki, T., Imada, M., Miyahara, M., Fujii, G.: Biomed., Pharamacother 39, 372 (1985)); and a line of mouse hybridoma cells having almost no substrate adherence (a hybridoma having mother cell from mouse myeloma of the strain X63-Ag8-6.5.3.: M. Miyahara unpublished) were cultivated. The assembly of the culture equipment, cell-seeding method and the counting method of cell numbers were conducted in accordance with those for the above mentioned huH-1 cells.

A line of C127I cells was cultivated in a growth medium consisting of Dulbecco's Modified Eagle's Medium (DME) supplemented with 5% fetal bovine serum. The cells were seeded at the density of $1.1 \times 10^4$ cells/cm$^2$ in terms of one surface of glass fiber. During the course of cultivation, the exchange ratio of culture medium was gradually raised, and the whole amount was changed daily after the 10th day. Glucose consumption rate increased up to the 14th day of culture to reach 60 mg/h per culture equipment and levelled off thereafter. At 23rd day of the culture, a cell density of $5-7 \times 10^5$/cm$^2$ in terms of one side of glass fiber was obtained. A line of KYM-1 human sarcoma cell was seeded at the density of $1.6 \times 10^5$ cells/cm$^2$ on the assumption that the glass fiber has two flat surfaces, and cultivated in a serum-free growth medium consisting of RPMI-1640 as the basal culture medium supplemented with trace components and 0.1% bovine serum albumin. Before seeding, the cells of this line showing very weak adherence had been maintained in suspension for generations. According to measurements 17 days after the start of culture, judging from the cell floating ratio, it was estimated that ca. 45% of cells were immobilized in the substratum at that stage. The change ratio of the culture medium was gradually increased during cultivation, and after the 17th day, daily 1000 ml of it was changed and the glucose concentration was maintained at 600 mg/l level. After 30 days of cultivation, cell a yield of $5.9 \times 10^5$/cm$^2$ in terms of the surface area of fabric was gained.

Mouse hybridoma cells of $2.2\times10^8$, which corresponded to the density of $7.3\times10^4$ cells/cm$^2$ surface area with the assumption that glass fiber is flat and two-sided. The cells were then cultivated in a growth medium consisting of RPMI-1640 culture medium supplemented with 10% FBS for 35 continuous days. During the culture duration, culture medium was changed in 0.59 volume/day up to the eleventh day of the culture and 0.89 volume/day thereafter. Glucose concentration was maintained 1.1–1.5 g/l. Judging from the glucose consumption, it can be said that this culture was stabilized after the 11th day. The density of suspended cells contained in culture medium drained during this period was around $5\times10^5$/ml. Cell density measured at the final stage of the culture was $6.3\times10^6$ ml per volume of substratum (equivalent to $6.3\times10^5$/cm$^2$ in terms of one side of glass fiber) showing that cells of about ten times the density of cells in suspension were stagnant in the substratum. Observation with a scanning electron microscope showed the hybridoma cells adhered to the surface of glass fibers or were immobilized by being stuck therebetween, and were fairly evenly distributed on the extensive area of the fiber.

The above mentioned results show that the cell culture equipment of the present invention (Example 1-type culture equipment) employing glass fiber as a material for substratum is applicable to immobilization, multiplication of cells, and maintenance of cultured cells of strong adherence to almost non-adherence.

EXAMPLE 2

In this example the cell cultures were made using type 4 culture equipment with ceramic substratum.

The line of mouse hybridoma and the conditions of culture medium were the same as those of the examples of practice using type 1 culture equipment. The ceramic substratum used in this practical example was 400 ml in volume and its surface area per unit volume is 20 cm$^2$/ml in terms of the ceramic surface regarded as flat. The surface density is twice the conversion surface density of glass fiber, which was used for type 1, 2 and 3 culture equipments. Hybridoma cells of $2.2\times10^8$ were seeded for the present culture equipment (equivalent to $3.7\times10^4$/cm$^2$ in terms of the ceramic surface regarded as flat,) and were cultivated continuously for 34 days in a growth medium consisting of RPMI-1640 culture medium supplemented with 10% FBS. During the continuous cultivation, the renewing rate of the culture medium was gradually raised up to the tenth day of the culture. Thereafter, it was maintained at 3.5 volume/day with the concentration of glucose ranging between 1.1–1.5 g/l. Judging from the consumption of glucose, this culture was almost stabilized after the eleventh day. The density of suspended cells contained in culture medium drained in the culture period was around $5\times10^5$/ml. The accurate measurement of cell density was not conducted at the final stage of the culture in this practice example, but judging from the production of their monoclonal antibody, we assume that the cell density of about four times that of the practical example using type 1 culture equipment was attained. The above results show that honeycomb-like ceramics are usable for substratum of the culture equipment of the present invention and are able to immobilize the cells having extremely weak substrate adherence, such as hybridoma cells.

EXAMPLE 3

This example was a scale-up using type 2 and 3 culture equipments with glass made substratum.

Tests of scaled up type 2 culture equipment (10 liter scale) and type 3 culture equipment (50 liter scale) were carried out using a line of human hepatic cancer cells huH-1 and a line of human rhabdomyosarcoma cells KYM-I as follows. Fundamentally, type 2 culture equipment is composed of similar parts as those of said type 1 culture equipment. Culture vessel 1 is made of polycarbonate with internal diameter of 30 cm and the depth of 17 cm and with outer jacket made of polycarbonate to keep warm. The lid 2 was a disc made of stainless steel having the same seven openings as the type 1 culture equipment. The stainless steel tubes and electrodes leading to these openings are the same as those aforementioned. Substratum support 10 was made of stainless steel with 10 cm height, and the central cylindric body 5 thereof has an internal diameter of 7 cm, to the top and to the bottom of which eight guides 6,6' are radially arranged, respectively. The substratum 4 is fixed to the substratum support 10 wrapped around manner as previously explained, with glass fiber cloth of 8.5 cm $\times$ 30 m wrapped at a 2 mm spacing. Its surface area is 51,000 cm$^2$ interms of area of both surfaces regarded flat. Conical-shaped circulation-generating room 13 was made of stainless steel. The arrangement of rotator 15 is the same as that of type 1 culture equipment previously said. The gas exchange of culture medium 3 can also be done through the coiled gas exchange unit of gas permeable teflon tube of 19 m attached to the bottom surface of the support of substratum 10.

In the test using huH-1 cells, cell culture was carried out under the same conditions of cells and multiplication culture medium as those of type 1 culture equipment previously mentioned, except that the micro-carrier culture was employed for cultivating seed cells to obtain $2.0\times10^9$ seed cells. The seed cells obtained were seeded in culture vessel 1 filled with 10 liter of culture medium. Then, culture was continued for 28 liter of culture medium. Then, culture medium at from 500 to 800 r.p.m. During the cultivation, in addition to aeration of air supplemented with 5% carbon dioxide gas, oxygen gas was supplied in the same manner as for the type 1 culture equipment. Renewal of culture medium was not performed for the initial four days. In the 27 days of culture duration thereafter, the total volume of culture medium was changed on occasion so as to maintain glucose level at 400 mg/l or above and lactic acid level at 800 mg/l or below. The yield of cells was $3.64\times10^5$/cm$^2$ per area. This value is almost equivalent to that obtained using CELL FACTORY ®.

For the type 3 culture equipment (50 liter capacity), a substratum was employed, wherein a glass fiber of 10 cm width and 180 m length was wrapped at 2 mm around spacing around a 12-angled stainless steel support of 60 cm diameter with a cylindrical opening in the center. The diameter of culture vessel was 60 cm, the depth, the internal volume of the vessel excluding lid, and the volume of substratum portion were 20 cm, 50 liters and 25 liters, respectively. Whereas for supporting the substratum in types 1 and 2 equipment (800 ml and 10 liter capacity), a combination of the arms composed of two parallel stainless steel bars and the pin-shaped spacers inserted therebetween was adopted, for type 3 equipment, the substratum was made by inserting the spacers, into the arm comprising one stainless bar with the glass fiber being wrapped around as previously explained. Each spacer included a pair of holes drilled near both ends of a stainless steel square bar of 5 mm with 2 mm thickness and 11 cm length. The surface area of the glass fiber with auxiliary clamps for fixing the spacers toward the outer rim attached, so as to stretch the wrapped fiber after completion of wrapping work, was 360,000 cm$^2$ in terms of one surface regarded as flat.

A line of human rhabdomyosarcoma cells (KYM-I) was used for this example. Suspension culture cells of $3 \times 10^{10}$ were seeded. After cultivation for 24 hours, the number of cells remaining in suspension was counted to be $4.7 \times 10^7$, by which it was estimated that the cells of 98% and more attached to substratum. The culture was carried on using serum-free growth medium previously said, with the continuous renewal of culture medium for 16 days. During this period, glucose level was maintained 500-1000 mg/l, and culture medium totaling 720 liter was supplied. Total numbers of cells were $1.87 \times 10^{11}$ at the completion of the culture. This value gives $5.2 \times 10^5$/cm$^2$ in terms of one surface of the glass fiber to be flat, equivalent to the cell density in monolayer culture. Cell suspended in the culture medium at the final stage of the culture was less than 0.2% of total cell numbers.

Although not described in detail, KYM-I cells excreted useful substances in the supernatant of the culture. Cellular DNA is a contaminant causing additional burden at the separation and purification phase of useful substances, however the supernatant produced with the present culture equipment contains only less than one-tenth (1/10) of the DNA contents contained in the supernatant obtained through the suspension culture. This fact means that the present culture equipment causes only a little damage to the cell, and that there are less chances for cellular substances to contaminate the supernatant of culture.

Meanwhile, the experiment for the human hepatic cancer cell huH-1 was successfully conducted as will be described for the long-term cultivation in example 4.

As seen in the above mentioned examples, the culture equipment according to the present invention could be easily expanded to 50 liter scale.

EXAMPLE 4

This example was a test of long term cultivation.

Conditions on cells and growth medium were the same as those in cell culture using said 800 ml culture equipment. For the seed of a line of huH-1 cells, cells were grown in monolayer in plastic dishes. It was treated with trypsin to obtain $3.0 \times 10^8$ seed cells, which were seeded in culture vessel 1 filled with 800 ml growth medium. Then the cells were adhered to substratum 4 through circulating culture medium 3 by virtue of rotation of rotator 15. The culture medium was not renewed for the initial two days, thereafter it was changed continuously in the range from 650 ml/day to 1,950 ml/day during 19 days in growing stage. After the 19th day, culture medium was changed to a serum-free culture medium consisting of William E culture medium as the main component. The serum-free culture was maintained for six months. During this period, oxygen was supplied on occasion in addition to the aeration of air supplemented with 5% carbon dioxide gas at the rate of 90-95 ml/min. By stereoscopic observation through the wall of culture vessel, we confirmed that the cells formed dense layers adhering to substratum 4 during the culture period.

During six months of cultivation, the stability in the viable state of cells was confirmed. From the cell numbers counted after the completion of the culture, the cell density of $4.4 \times 10^7$/cm$^3$ in terms of that per volume of substratum 4 was attained. This equals $5.8 \times 10^6$/cm$^2$ in terms of the calculation of the cell density per unit area of the fabric from the both side surfaces used for substratum 4. This value is 10 times the cell density accomplished in culture using CELL FACTORY®. This ratio shows that the culture equipment of the present invention is very effective as a system for substance production.

A long term culture test was carried out using human hepatic cancer huH-1 cell in type 3 culture equipment (scaled up to 50 liter). The specification of the type 3 culture equipment was basically the same as that of the aforementioned one, except for the addition of two gas exchange cylinders connecting in each cylinder contained a silicon tubular thread of 2 cm in diameter and 26 cm in length and with bundles of silicon hollow fiber. A part of the culture medium was circulated by a peristaltic pump in a gas exchange cylinder in order to enhance gas exchange efficiency. It was structured so that 100% oxygen supply to the silicon tubular thread was secured. This gas exchange apparatus was not used at an early stage of cultivation, but was used after the oxygen pressure of culture medium lowered due to an increase of cell numbers. In this example of practice, cells of $5.9 \times 10^9$ were inoculated and maintained for 209 days in culture. For the initial 26 days, DM-160 culture medium supplemented with 5% bovine fetal serum was used to make cells grow. After this step, culture medium was changed to serum-free medium consisting mainly of Williams E medium as described for the practical example for type 1 culture equipment. No troubles were observed in the culture equipment during total 209 days. $2.2 \times 10^{11}$ cells were collected. This amount of cells gives the density of $9 \times 10^6$/cm$^3$ in terms of the density per volume of substratum, whereas $9 \times 10^5$ cells/cm$^2$ in terms of the density per one surface of the glass fiber. Although this value is lower than the density achieved by type 1 culture equipment, it is 1.8 timer higher than the density by CELL FACTORY®. The cell line used in this example also produced useful substances. In comparison with the value achieved by CELL FACTORY®, productivity of a single set of the present culture equipment is as high as that of 130 to 140 sets of CELL FACTORY with 6,000 cm$^2$ culture surface area and capable of accommodating 1 liter of culture medium.

EXAMPLE 5

In this example the gas exchange performance on the liquid surface of the present invention was measured. Permeability was measured for oxygen gas on liquid surface using the type 3 culture equipment (50 liter). The glass fiber substratum was loaded into the 50 liter culture equipment, and the vessel was filled with distilled water, and then was circulated by stirrer. Immediately before the measurement, sodium sulfite was added followed by adjustment of oxygen pressure to zero, by putting the lid over the culture equipment. The rise in oxygen pressure was measured using an oxygen electrode with air, or mixed gas of air and oxygen gas being aerated over the surface of liquid. In this measurement, circulation was not facilitated actively using a device such as surface aeration fan. However, maximum efficiency of apparent oxygen absorption was about 800 mg per hour in the state of the aeration of 100% oxygen gas.

Assuming that the oxygen consumption rate of normal cells is 2 $\mu g/10^6$ cells/hour, the maximum number of cells per one culture equipment of $4 \times 10^{11}$, the maximum cell density of $1.6 \times 10^7/cm^2$ per substratum volume, or of $1.6 \times 10^6/cm^2$ per area in terms of the glass fiber surface regarded as flat, can be expected from this value, on condition of surface aeration without particular acceleration. These values give a base to estimate maximum cell density in the present culture equipment without auxiliary apparatus for gas exchange. A higher cell density due to the relatively high rate of circulation can be expected from the small equipments type 1 and 2.

Although no details have been given in this example, axenic collection of grown cells attaching to glass fiber is possible. In case of the human hepatic cancer cells huH-1, 96% of cells were collected in suspending solution by applying mechanical shock several times to fiber substratum from outside of culture vessel after trypsin treatment.

As seen in the examples described above, the circulatory culture equipment according to this invention has many merits as follows: 1) Unlike prior culture methods such as micro-carrier culture method and suspension culture method, the culture method of present invention causes little mechanical damage to cultured cells. 2) Unlike monolayer culture methods and micro-carrier culture methods, the culture of present invention causes little detaching, moving, or uneven distribution of cells cultivated, so that long-term stable maintenance can be possible. 3) Regardless of the strength of the cell adhesiveness, various cells can be cultivated with the present equipment. 4) Unlike micro-carrier culture methods, suspension culture methods, and hollow fiber culture methods, an exogenous gas exchanger is not essential in this culture method. 5) Unlike suspension culture methods and micro-carrier culture methods, no apparatus for isolating cells from culture medium is needed in this culture method. 6) Unlike suspension culture methods and micro-carrier culture methods, there is only a small amount of contaminant cell substance in the supernatant of a culture solution using this equipment. 7) Unlike hollow fiber culture methods, the culture method using this equipment needs no large loading on pump. Unlike micro-carrier culture methods and suspension culture methods, the reliability in gas exchange apparatus and cell separator according to the present invention is high so as to cause no anxiety.

Unlike micro-carrier culture equipment, suspension culture equipment, and hollow fiber culture equipment, the present culture equipment needs no culture medium circulation system outside culture equipment so that it is operated as an integrated system. The high reliability in biological containment thus leads to a high reliability in the total equipment. 8) The volume of unit culture equipment, which frequently causes problems with the culture of adherent cells, is compact and easy to control, resulting in high reliability in the culture equipment of the present invention, and in economy as a culture equipment stands for a long life.

What is claimed is:

1. A circulatory culture apparatus for cultivating cells, comprising:
   a culture vessel having an open top;
   a lid for enclosing said open top;
   a substratum comprising a strip of material, to which cells adhere and immobilize, which is spirally or concentrically wrapped around a frame means for supporting said strip of material with a distance maintained between adjacent layers of the wrapped material, disposed within said vessel, wherein said distance between adjacent layers defines a plurality of first spaces for permitting circulation of a culture medium by ascent of the medium therethrough; said substratum being configured such that a second space is defined by a space which is not occupied by said wrapped material for permitting circulation of the culture medium by descent of the medium therethrough;
   a circulation-inducing chamber disposed within said vessel, below said substratum and communicating with said first spaces and said second space;
   rotator means disposed within said circulation-inducing chamber and below said second space for imparting centrifugal force to said culture medium and for circulating the culture medium through said first spaces in said culture vessel; and
   a gas phase space defined between said lid and said substratum, said gas phase space being adapted for gas exchange between the culture medium and gas within said gas phase space.

2. A circulatory culture apparatus for cultivating cells, comprising:
   a generally cylindrical vessel having an open top and a closed bottom and adapted for the circulation of a culture medium therein;
   a lid for enclosing said open top;
   a substratum disposed within the vessel and adapted for the growth of cell cultures thereon, said substratum defining at least one central vertical passage and a plurality of additional vertical passages radially spaced outward from the central vertical passage;
   a wall portion extending upwardly from the bottom of the vessel to the central vertical passage to define a circulation-inducing chamber communicating with said central vertical passage, said wall portion having a plurality of openings for the passage of the culture medium therethrough;
   rotator means disposed within the circulation-inducing chamber for circulating the culture medium throughout the vessel, such that rotation of the rotator means draws the culture medium down the central vertical passage into said chamber wherein centrifugal force is imparted to the medium by the rotator means and the medium flows out said openings and up through the radially spaced vertical passages in the substratum;
   a gas phase space defined between said lid and said substratum, said gas phase space being adapted for gas exchange between the culture medium and gas within said gas phase space,
   wherein said lid has a gas inlet and a gas outlet, whereby gas exchange occurs between gas supplied through the inlet and gases contained in the culture medium as it flows out of said radially spaced passages, through the gas phase space and into the central vertical passage; and
   means for facilitating circulation of gases in the gas phase space, including a member secured to and spaced away from said lid and defining a central opening for circulation of gasses therethrough.

3. The apparatus according to claim 2, wherein said wall portion defines a frusto-conical circulation-inducing chamber such that the rotational movement of the medium within the chamber is substantially unimpeded.

4. The apparatus according to claim 2, further comprising:
- a cylindrical wall surrounding the substratum and defining an annular space between said wall and the vessel for receiving an amount of the circulating culture medium, said wall having a portion extending a predetermined distance beyond the substratum in the direction of the vessel top; and
- means communicating with the gas phase space for allowing a predetermined amount of culture medium from the annular space to flow into the gas phase space.

5. The apparatus according to claim 2, further comprising means for supporting the substratum including a central tubular member for defining the central vertical passage and arm members radially extending from the central tubular member.

6. The apparatus according to claim 5, wherein the substratum comprises a strip of material secured to said support means and wrapped around the circumference of the central tubular member to form a plurality of adjacent layers of said strip of material, said adjacent layers being spaced apart by spacer means mounted on the radial arms to define the radially outward vertical passages of the substratum.

7. A circulatory culture apparatus for cultivating cells, comprising:
- a culture vessel having an open top;
- a lid for enclosing said open top;
- a substratum comprising a strip of wrapped material, to which cells adhere and immobilize, which is spirally or concentrically wrapped around a frame means for supporting said strip of material with a distance maintained between adjacent layers of the wrapped material, disposed within said vessel, wherein said distance between adjacent layers defines a plurality of first vertical spaces for permitting circulation of a culture medium by ascent of the medium therethrough; a central part of said substratum not occupied by said wrapped material defining a second vertical space for permitting circulation of the medium by descent of the medium therethrough;
- a circulation-inducing chamber defined by a wall extending upwardly from the bottom of the vessel to the central part of the substratum, said wall having a plurality of openings for the passage of the culture medium therethrough for communicating with said first vertical spaces and said second vertical space;
- rotator means disposed within the circulation-inducing chamber for circulating the culture medium throughout the vessel by imparting centrifugal force to said culture medium to draw the culture medium down the second vertical space into said chamber and to expel the medium through said openings and force up through the first vertical spaces in the substratum; and
- a gas phase space defined between said lid and said substratum, said gas phase space being adapted for gas exchange between the culture medium and gas within said gas phase space.

8. The apparatus according to claim 7, wherein said central part is defined by a central hollow tube, said strip of material being wrapped around the circumference of said tube.

9. The circulatory culture apparatus of claim 7, further comprising a disk-shaped circulation-guiding plate having holes in the center placed in said gas phase space.

* * * * *